(12) United States Patent
Hata et al.

(10) Patent No.: US 11,944,283 B2
(45) Date of Patent: Apr. 2, 2024

(54) MEDICAL APPARATUS AND ADHESION PROMOTING DEVICE USING SAME

(71) Applicant: TERUMO KABUSHIKI KAISHA, Tokyo (JP)

(72) Inventors: Mayu Hata, Kanagawa (JP); Miho Kai, Kanagawa (JP); Naoki Aramaki, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 446 days.

(21) Appl. No.: 16/987,897

(22) Filed: Aug. 7, 2020

(65) Prior Publication Data
US 2020/0360002 A1    Nov. 19, 2020

Related U.S. Application Data

(63) Continuation of application No. PCT/JP2019/004690, filed on Feb. 8, 2019.

(30) Foreign Application Priority Data

Feb. 8, 2018  (JP) .................................. 2018-021171

(51) Int. Cl.
*A61B 17/00*    (2006.01)
*A61B 17/11*    (2006.01)
*A61L 31/04*    (2006.01)

(52) U.S. Cl.
CPC ...... *A61B 17/0057* (2013.01); *A61B 17/1114* (2013.01); *A61L 31/042* (2013.01);
(Continued)

(58) Field of Classification Search
CPC .............. A61B 17/0057; A61B 17/04; A61B 17/07292; A61B 17/1114;
(Continued)

(56) References Cited

U.S. PATENT DOCUMENTS

| 2003/0171823 A1* | 9/2003 | Zotti ..................... A61F 2/0063 623/23.72 |
|---|---|---|
| 2005/0059996 A1 | 3/2005 | Bauman et al. |

(Continued)

FOREIGN PATENT DOCUMENTS

| CN | 101932344 A | 12/2010 |
|---|---|---|
| JP | 01274750 A | 11/1989 |

(Continued)

OTHER PUBLICATIONS

International Search Report (PCT/ISA/210) dated May 7, 2019, by the Japan Patent Office as the International Searching Authority for International Application No. PCT/JP2019/004690.
(Continued)

*Primary Examiner* — Mohamed G Gabr
(74) *Attorney, Agent, or Firm* — BUCHANAN INGERSOLL & ROONEY PC

(57) ABSTRACT

To reduce the risk of a ruptured suture after a surgery or the like, a medical apparatus includes a biodegradable sheet in which a plurality of through-holes are formed, a value of a ratio (D/P) of a hole diameter D to a pitch P of the through-hole is in a range of 0.25 or more and less than 40. Such a medical apparatus is useful as an adhesion promoting device for promoting adhesion of biological tissue.

21 Claims, 6 Drawing Sheets

(52) U.S. Cl.
CPC ... *A61L 31/043* (2013.01); *A61B 2017/00597* (2013.01); *A61B 2017/0065* (2013.01)

(58) Field of Classification Search
CPC .......... A61B 2017/00004; A61B 2017/00597; A61B 2017/0065; A61B 2017/00884; A61B 2017/00893; A61B 2017/00951; A61B 2017/0495; A61B 2017/1132; A61B 2017/1135; A61F 2/0063; A61F 2/04; A61F 2210/0004
See application file for complete search history.

(56) References Cited

U.S. PATENT DOCUMENTS

| | | |
|---|---|---|
| 2006/0073182 A1 | 4/2006 | Wong et al. |
| 2006/0085030 A1 | 4/2006 | Bettuchi et al. |
| 2006/0085034 A1 | 4/2006 | Bettuchi |
| 2006/0108393 A1 | 5/2006 | Heinrich et al. |
| 2007/0203510 A1 | 8/2007 | Bettuchi |
| 2008/0287961 A1 | 11/2008 | Miyamoto et al. |
| 2009/0069904 A1 | 3/2009 | Picha |
| 2009/0216338 A1* | 8/2009 | Gingras ................ A61F 2/0077 623/23.72 |
| 2009/0318843 A1 | 12/2009 | Van Holten et al. |
| 2010/0012703 A1 | 1/2010 | Calabrese et al. |
| 2010/0015200 A1 | 1/2010 | Mcclain et al. |
| 2010/0312043 A1* | 12/2010 | Goddard ............... A61F 2/0045 600/30 |
| 2011/0262696 A1* | 10/2011 | Bayon ................... A61F 2/0045 428/131 |
| 2011/0288568 A1* | 11/2011 | Capuzziello .......... A61F 2/0063 606/151 |
| 2013/0204078 A1 | 8/2013 | Li et al. |
| 2014/0044861 A1 | 2/2014 | Boey et al. |
| 2015/0351753 A1 | 12/2015 | Shelton et al. |

FOREIGN PATENT DOCUMENTS

| | | |
|---|---|---|
| JP | 2004509205 A | 3/2004 |
| JP | 2006110356 A | 4/2006 |
| JP | 2007505708 A | 3/2007 |
| JP | 2007229457 A | 9/2007 |
| JP | 2008-516669 A | 5/2008 |
| JP | 2008514719 A | 5/2008 |
| JP | 2011015966 A | 1/2011 |
| JP | 2011528275 A | 11/2011 |
| JP | 2012517319 A | 8/2012 |
| JP | 2017521134 A | 8/2017 |
| JP | 2018-202003 A | 12/2018 |
| WO | 2005027983 A2 | 3/2005 |
| WO | 2008001952 A1 | 1/2008 |
| WO | 2010/052584 A2 | 5/2010 |
| WO | 2018/025212 A1 | 2/2018 |

OTHER PUBLICATIONS

Written Opinion (PCT/ISA/237) dated May 7, 2019, by the Japan Patent Office as the International Searching Authority for International Application No. PCT/JP2019/004690.

Extended European Search Report dated Oct. 26, 2020 issued by the European Patent Office in corresponding European Patent Application No. 19750339.4 (12 pages).

An English Translation of the International Search Report (Form PCT/ISA/210) and the International Preliminary Report on Patentability (Form PCT/IPEA/409) dated May 7, 2019, by the Japanese Patent Office in corresponding International Application No. PCT/JP2019/004690. (8 pages).

Office Action (Notice of Reasons for Refusal) dated Sep. 6, 2022, by the Japan Patent Office in corresponding Japanese Patent Application No. 2019-571175 and an English Translation of the Office Action. (10 pages).

Office Action (The First Office Action) dated Apr. 14, 2023, by the National Intellectual Property Administration, P. R. China in corresponding Chinese Patent Application No. 201980010657.7 and an English translation of the Office Action. (14 pages).

Office Action (Notice of Reasons for Refusal) dated Jan. 9, 2024, in corresponding Japanese Patent Application No. 2023-060201 and English translation of the Office Action. (8 pages).

* cited by examiner

MEDICAL APPARATUS AND ADHESION PROMOTING DEVICE USING SAME

CROSS-REFERENCES TO RELATED APPLICATIONS

This application is a continuation of International Patent Application No. PCT/JP2019/004690 filed on Feb. 8, 2019, which claims priority to Japanese Patent Application No. 2018-021171 filed on Feb. 8, 2018, the entire content of both of which is incorporated herein by reference.

FIELD OF THE INVENTION

The present invention is a medical apparatus and an adhesion promoting device using the same.

BACKGROUND DISCUSSION

The surgical indication of a surgery is determined in each individual by comparing a benefit derived from the surgery with a surgical wound (a wound such as an incisional wound and an anastomotic wound) or surgical invasiveness. That is, the surgery is performed in a case where the benefit of the surgery surpasses the detriment of the surgical invasion (surgical indication). Therefore, in a case where the benefit derived from the surgery is large, but a living body is not likely to withstand the surgical invasion and to recover, the surgery is not performed (contraindication). However, in practice, there are many cases where it is difficult to weigh the detriment of the surgery due to damage and the benefit of the surgery, and there are many cases where it is not possible to optimistically view the situation even in a case where the surgery appears to be beneficial before the surgery (with surgery indication). This is caused by many factors existing before the surgery, during the surgery, and after the surgery, and is affected by a variety of factors such as individual strength and immunity of the patient, cardiopulmonary function, and infection, and thus, an unexpected result of the surgery may be obtained. For example, on an anatomical form, in surgery of the digestive canal (subtotal esophagectomy to address esophagus cancer, pancreatoduodenectomy to address pancreatic cancer, colectomy to address colorectal cancer, and the like) in which circulation disorder is easily caused and there is no means for improving circulation, when a ruptured suture occurs at a suture site, contents are leaked from a ruptured anastomosis site, and thus, inflammation may be caused. Then, an inflammation symptom such as fever is caused, and, in a critical case, a fatal complication such as peritoneum inflammation or ichorrhemia may occur, and abrosia or antibacterial agent delivery, and a reoperative surgery may be required.

As described above, in particular, in a surgery for the digestive canal, the most important prognosis determination factor is that wound healing (adhesion) at the anastomosis site is not delayed.

To prevent the occurrence of such a ruptured suture, for example, in colorectal cancer that is known to have a high occurrence rate of the ruptured suture (in particular, lower advanced rectal cancer), in order to reduce the influence of a surgery factor in the causes of the ruptured suture, an anastomotic method has been considered in which blood flow is maintained, and an excessive tension is not applied. In addition, many proposals for reducing the risk of the ruptured suture by performing stapled anastomosis using an anastomotic appliance such as a circular stapler have been made (for example, refer to JP-T-2007-505708 (the term "JP-T" as used herein means a published Japanese translation of a PCT patent application) (WO 2005/027983 A)).

SUMMARY

However, even in a case of using the stapled anastomosis as described in JP-T-2007-505708 (WO 2005/027983 A), the degree of progress of the wound healing (the adhesion) at the anastomosis site depends on a patient factor such as a tissue state of a patient, and thus, the risk of the ruptured suture still remains. In addition, it is necessary for an operator to be skilled in the manipulation or use of a dedicated anastomotic appliance in order to perform the stapled anastomosis, and thus, it is difficult to say that such a method represents a simple solution.

The medical device disclosed here is able to reduce the risk of a ruptured suture after a surgery or the like by a relatively simple technique.

The inventors have conducted intensive studies about reducing the risk of a ruptured suture after a surgery or the like. As a result, the inventors have discovered that wound healing (adhesion) in an anastomosis site at a surgery or the like is promoted by using a biodegradable sheet having a plurality of through-holes of which the profile of a hole diameter and a pitch is controlled.

That is, according to one aspect, a medical apparatus including a biodegradable sheet in which a plurality of through-holes are formed is provided. Here, a value of a ratio (D/P) of a hole diameter D to a pitch P of the through-hole is controlled in a range of 0.25 or more and less than 40. The medical apparatus is preferably used as an adhesion promoting device that is used for promoting the adhesion of a biological tissue.

According to another aspect, an adhesion promoting medical device configured to be positioned at an anastomosis site in a living body comprises: a biodegradable sheet fabricated from a biodegradable resin, with the biodegradable sheet possessing opposite surfaces and including a plurality of spaced-apart through-holes passing through the biodegradable sheet so that the plurality of spaced-apart through-holes open to the opposite surfaces of the biodegradable sheet. The biodegradable sheet also possesses an outer periphery, with the plurality of through-holes being spaced inwardly from the outer periphery of the biodegradable sheet. Each of the through-holes possesses a hole inner diameter D and an outer periphery, and a straight line distance between the outer periphery of each of the plurality of spaced-apart through-holes and an adjacent one of the plurality of spaced-apart through-holes is a pitch P of the through-hole. The ratio (D/P) of the hole inner diameter D to the pitch P of each of the plurality of spaced-apart through-holes is 0.25 or more and less than 40, and application of the adhesion promoting device to an anastomosis site causes a biological reaction to induce expression of a biological component which accumulates through the plurality of spaced-apart through-holes to thereby promote adhesion at the anastomosis site.

According to a further aspect, a method comprises: positioning a biodegradable sheet at an anastomosis site following a surgical procedure; wherein the biodegradable sheet that is positioned at the anastomosis site possesses opposite surfaces and includes a plurality of spaced-apart through-holes passing through the biodegradable sheet so that the plurality of spaced-apart through-holes open to the opposite surfaces of the biodegradable sheet, with each of the plurality of the through-holes possessing a hole inner diameter D, and a straight line distance between the outer periphery of each of the plurality of spaced-apart through-holes and an adjacent one of the plurality of spaced-apart through-holes being a pitch P of the through-hole. The biodegradable sheet that is positioned at the anastomosis site is configured so that a ratio (D/P) of the hole inner diameter D to the pitch P of each of the plurality of through-holes is 0.25 or more and less than 40; and the biodegradable sheet that is positioned at the anastomosis site causing a biological reaction that induces expression of a biological component that is accumulated through the through-holes to promote adhesion at the anastomosis site.

DETAILED DESCRIPTION

Figure 1:
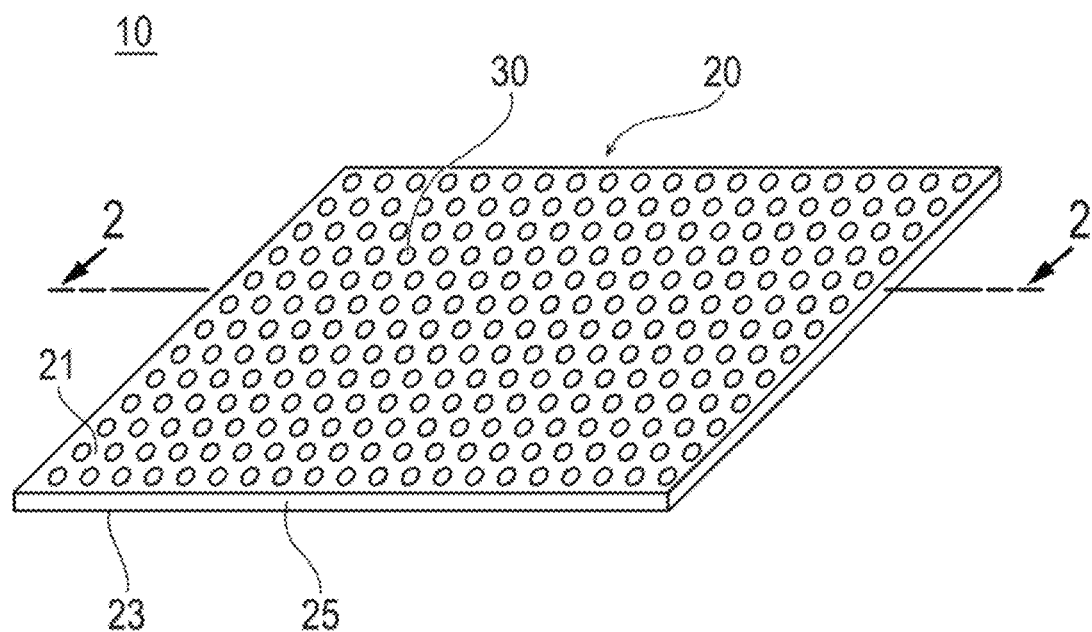
FIG. 1 is an overview perspective view of a biodegradable sheet constituting a medical apparatus according to one embodiment disclosed here by way of example.

Set forth below with reference to the accompanying drawings is a detailed description of embodiments of a medical apparatus and adhesion promoting device representing examples of the inventive medical apparatus and adhesion promoting device disclosed here.

<<Medical Apparatus (Biodegradable Sheet)>>

As described above, one aspect of the disclosure here relates to a medical apparatus including a biodegradable sheet in which a plurality of through-holes are formed, in which a value of a ratio (D/P) of a hole diameter (hole inner diameter) D to a pitch P of the through-hole is 0.25 or more and less than 40. The medical apparatus according to this aspect makes it possible to reduce the risk of a ruptured suture after a surgery or the like by a simple technique of interposing the medical apparatus between anastomosis sites (suture sites). Hereinafter, this aspect will be described in detail.

The medical apparatus according to this aspect includes the biodegradable sheet.

<Constituent Material of Biodegradable Sheet>

A constituent material of the biodegradable sheet is not particularly limited, and examples of the constituent material of which the biodegradable sheet is made include a biodegradable resin. For example, a known biodegradable (co)polymer described in JP-T-2011-528275, JP-T-2008-514719, WO 2008-1952 A, JP-T-2004-509205, and the like can be used as the biodegradable resin. Specifically, examples of the biodegradable resin include (1) a polymer selected from the group consisting of aliphatic polyester, polyester, polyacid anhydride, polyorthoester, polycarbonate, polyphosphazene, polyphosphoric acid ester, polyvinyl alcohol, polypeptide, polysaccharide, protein, and cellulose; (2) a copolymer containing one or more monomers configuring (1) described above, and the like. That is, it is preferable that the biodegradable sheet contains at least one type of biodegradable resin selected from the group consisting of the polymer selected from the group consisting of the aliphatic polyester, the polyester, the polyacid anhydride, the polyorthoester, the polycarbonate, the polyphosphazene, the polyphosphoric acid ester, the polyvinyl alcohol, the polypeptide, the polysaccharide, the protein, and the cellulose, and the copolymer containing one or more monomers configuring the polymer.

Here, the aliphatic polyester is not particularly limited, and examples of the aliphatic polyester include a polylactic acid (PLA) such as a poly-L-lactic acid, a poly-D-lactic acid, and a poly-DL-lactic acid, a polyglycolic acid (PGA), a polyhydroxybutyric acid, a polyhydroxyvaleric acid, a polyhydroxypentanoic acid, a polyhydroxyhexanoic acid, a polyhydroxyheptanoic acid, polycaprolactone, polytrimethylene carbonate, polydioxanone, a polymalic acid, polyethylene adipate, polyethylene succinate, polybutylene adipate, polybutylene succinate, and the like. In addition, the polycarbonate is not particularly limited, and examples of the polycarbonate include tyrosine-derived polycarbonate and the like.

Alternatively, the biodegradable resin configuring the biodegradable sheet may contain a copolymer in which monomers configuring a polymer are arbitrarily copolymerized. Here, the copolymer is not particularly limited. Specifically, examples of the copolymer include a lactic acid-caprolactone copolymer, a caprolactone-glycolic acid copolymer, PLGA (poly(lactide-co-glycolide), polyanhydride, polyorthoester, poly(N-(2-hydroxypropyl) methacrylamide), DLPLA-poly(dl-lactide), LPLA-poly(l-lactide), PGA-polyglycolide, PDO-poly(dioxanone), PGA-TMC-poly(glycolide-co-trimethylene carbonate), PGA-LPLA-poly(l-lactide-co-glycolide), PGA-DLPLA-poly(dl-lactide-co-glycolide), LPLA-DLPLA-poly(l-lactide-co-dl-lactide), and PDO-PGA-TMC-poly(glycolide-co-trimethylene carbonate-co-dioxanone)), and polyanhydrideesters (PAE)-salicylate in which a salicylic acid is chemically introduced into a polymer main chain (for example, a polymer in which a salicylic acid is bonded to both terminals of a polylactide anhydride or a polyadipic acid), and the like.

The polymers and the copolymers described above may be respectively independently used, two or more types of the polymers/copolymers described above may be used by being combined, or one or more types of polymers and one or more types of copolymers may be used by being combined. In addition, the polymers and the copolymers described above may be respectively produced by synthesis or commercially available products may be used. A synthesis method is not particularly limited, and a known method can be similarly applied or can be applied by being suitably modified. For example, the polylactic acid (PLA), the polyglycolic acid (PGA), or the lactic acid-glycolic acid copolymer (PLGA) can be obtained by selecting a material having a required structure from an L-lactic acid, a D-lactic acid, and a glycolic acid, as a raw material, and by performing dehydration polycondensation. Preferably, the polylactic acid (PLA), the polyglycolic acid (PGA), or the lactic acid-glycolic acid copolymer (PLGA) can be obtained by selecting a material having a required structure from lactide that is a cyclic dimer of a lactic acid and glycolide that is a cyclic dimer of a glycolic acid, and by performing ring-opening polymerization. The lactide includes L-lactide that is a cyclic dimer of an L-lactic acid, D-lactide that is a cyclic dimer of a D-lactic acid, meso-lactide in which a D-lactic acid and an L-lactic acid are subjected to cyclic dimerization, and DL-lactide that is a racemic mixture of the D-lactide and the L-lactide. In the medical device disclosed here, any lactide can be used.

A weight average molecular weight of the biodegradable resin is not particularly limited insofar as a moderate biodegradation rate can be exhibited. Specifically, it is preferable that the weight average molecular weight of the biodegradable resin is 10,000 or more. That is, it is preferable that the biodegradable sheet contains a biodegradable resin having a weight average molecular weight of 5,000 or more. The weight average molecular weight of the biodegradable resin according to the invention is more preferably 8,000 to 200,000, and is even more preferably 10,000 to 150,000. A measurement method for determining the weight average molecular weight is a gel permeation chromatography (GPC).

In the biodegradable resins described above, the polylactic acid (PLA), the polyglycolic acid (PGA), the polycaprolactone, the lactic acid-caprolactone copolymer, the caprolactone-glycolic acid copolymer, the lactic acid-glycolic acid copolymer (PLGA), the tyrosine-derived polycarbonate (tyrosine-polycarbonate), the polyanhydride esters (PAE)-salicylate are preferable, and the PLA, the PGA, or the PLGA is particularly preferable. This is because such biodegradable resins have high biocompatibility, and easily control decomposition in a living body. A copolymerization ratio of PGA/PLA in the PLGA is not particularly limited, but it is preferable that PGA/PLA is 50/50 or more and less than 100/0, in a molar ratio.

<Shape of Biodegradable Sheet>

Figure 2:
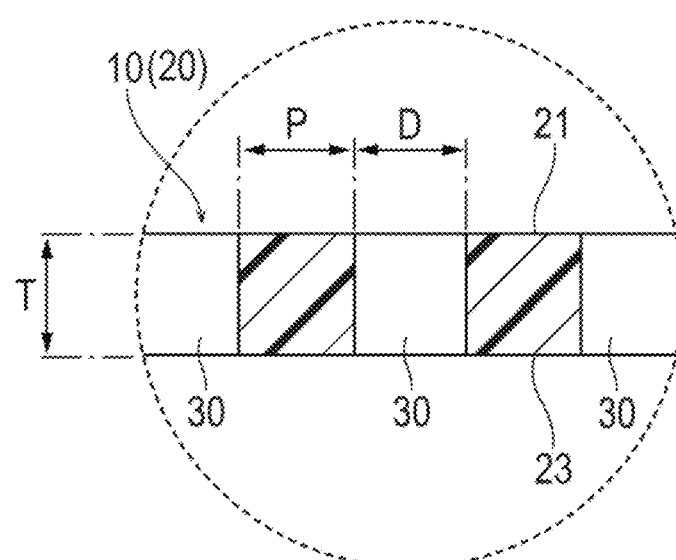
FIG. 2 is an enlarged view of a part of a sectional surface along the section line 2-2 in FIG. 1.
Figure 3:
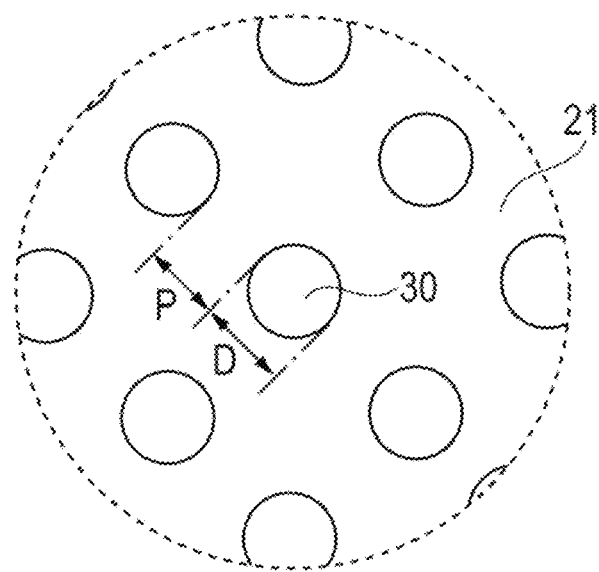
FIG. 3 is an enlarged view for describing the size of a plurality of through-holes, and is a plan view seen from a direction of the arrow 3 in FIG. 1.

FIG. 1 is a plan view of the biodegradable sheet constituting the medical apparatus according to one embodiment representing an example of the inventive biodegradable sheet/medical apparatus disclosed here. FIG. 2 is a sectional view along the section line 2-2 in FIG. 1. FIG. 3 is an enlarged explanatory diagram for describing the size of the plurality of through-holes.

As illustrated in FIG. 1, a biodegradable sheet 20 constituting a medical apparatus 10 is in the shape of a sheet. A plurality of through-holes 30 are formed in the biodegradable sheet 20. In FIG. 1, the plurality of through-holes 30 are regularly and periodically provided. The plurality of through-holes 30 may be randomly provided, and it is preferable that the plurality of through-holes are regularly and periodically provided. In addition, in FIG. 1, the plurality of through-holes 30 are provided perpendicularly along a thickness direction of the biodegradable sheet 20 (an up-down direction of FIG. 2). The plurality of through-holes 30 may be provided to be curved from an opening portion facing one surface (a front surface) 21 of the biodegradable sheet 20 towards an opening portion facing the other surface (a back surface) 23, and it is preferable that the plurality of through-holes are provided approximately perpendicularly along the thickness direction of the biodegradable sheet 20, and it is preferable that the plurality of through-holes are provided perpendicularly along the thickness direction of the biodegradable sheet 20. In the embodiment illustrated in FIG. 1, the through-holes 30 are spaced inwardly from the outermost periphery (lateral sides or lateral surfaces) of the biodegradable sheet 20 so that the through-holes do not intersect the periphery.

The thickness of the biodegradable sheet 20 (a size T illustrated in FIG. 2) is not particularly limited, but is preferably 0.05 mm to 0.3 mm, and is more preferably 0.1 mm to 0.2 mm. In a case where the thickness of the biodegradable sheet 20 is 0.05 mm or more (in particular, 0.1 mm or more), it is possible to ensure a sufficient strength to the extent that the biodegradable sheet is not broken at handling. On the other hand, in a case where the thickness of the biodegradable sheet 20 is 0.3 mm or less (in particular, 0.2 mm or less), it is possible to ensure sufficient flexibility for the biodegradable sheet to closely follow tissue to which the biodegradable sheet is applied.

As illustrated in FIG. 1, the biodegradable sheet 20 according to this embodiment has an approximately rectangular shape, in a plan view. However, the outer shape of the biodegradable sheet 20 is not particularly limited, and for example, may be a circular shape (refer to FIG. 7), an elliptical shape, or the like.

The biodegradable sheet 20 constituting the medical apparatus has a characteristic in the profile of the size of the plurality of through-holes 30. Specifically, the biodegradable sheet is characterized in that the value of the ratio of the hole inner diameter D (a distance or dimension D illustrated in FIG. 3) of the plurality of through-holes 30 to the pitch P (a distance (straight line distance) P illustrated in FIG. 3) of the plurality of through-holes 30 is 0.25 or more and less than 40. Here, in a case where the through-hole 30 is in the shape of a true circle, in a plan view, the hole diameter D of the through-hole 30 is identical to the diameter of the true circle. On the other hand, in a case where the through-hole 30 is not in the shape of a true circle, in a plan view, the diameter of the true circle (an equivalent circle diameter) having the same area as the area of the opening portion of the through-hole 30 is set to or identified as the hole diameter D of the through-hole 30. The biodegradable sheet 20 includes the plurality of through-holes 30, and thus, there are a plurality of values of the hole diameters D respectively corresponding to the through-holes 30. Therefore, in the calculation of the value of the ratio described above, an arithmetic average value of two or more of the values of the hole diameters D respectively corresponding to the plurality of through-holes 30 is used as a representative value of the hole diameter D. On the other hand, the "pitch P" of the plurality of through-holes 30 indicates the shortest distance between the opening portions of two through-holes 30. In the value of the pitch P, there are a plurality of values of the pitches P respectively corresponding to combinations of the adjacent through-holes 30. Therefore, in the calculation of the value of the ratio described above, an arithmetic average value of two or more of the values of the pitches P respectively corresponding to the combinations of the adjacent through-holes 30 is used as a representative value.

As described above, in this example of the medical apparatus and adhesion promoting device, it is essential that the value of the ratio (Hole Diameter/Pitch Ratio (D/P)) of the hole diameter D of the plurality of through-holes 30 to the pitch P of the plurality of through-holes 30 is 0.25 or more and less than 40. The value of the ratio (D/P) is preferably 0.5 to 35, is more preferably 1.0 to 30, and is even more preferably 1.5 to 20. Here, as a mechanism in which adhesion is promoted by the medical apparatus 10 (the biodegradable sheet 20) disclosed here, it is assumed that the constituent material configuring or constituting the biodegradable sheet 20, such as the biodegradable resin, causes a biological reaction, and thus, the expression of a biological component such as fibrin is induced, and the biological component that is induced as described above is accumulated through the through-hole of the biodegradable sheet to achieve the adhesion. Therefore, in a case where the value of the Hole Diameter/Pitch ratio (D/P) described above is excessively small (less than 0.25), the hole diameter is excessively relatively small with respect to the pitch, and thus, even in a case where the fibrin or the like is induced, the accumulation through both surfaces of the sheet by way of the through holes does not sufficiently occur, and it is not possible to promote the adhesion. On the other hand, in a case where the value of the Hole Diameter/Pitch ratio (D/P) described above is excessively large (40 or more), the pitch is excessively relatively small with respect to the hole diameter, and thus, it is not possible to sufficiently induce the biological component such as the fibrin, and it is not also possible to promote the adhesion.

A specific value of each of the hole diameter D and the pitch P is not particularly limited, but the hole inner diameter D is preferably 0.1 mm to 6 mm, more preferably 0.3 mm to 4 mm, and even more preferably 0.6 mm to 1.5 mm. In addition, the pitch P is preferably 0.1 mm to 0.4 mm, and more preferably 0.2 mm to 0.4 mm.

<Blend of Adhesion Enhancement Agent>

An adhesion enhancement agent for promoting the adhesion may be blended in the biodegradable sheet constituting the medical apparatus. The adhesion enhancement agent is not particularly limited insofar as a material has a synechia function in pleurodesis. Examples of the adhesion enhancement agent include talc, povidone-iodine (Isocline or the like), a curing agent (minocycline, tetracycline, or the like), a carcinostatic agent (adriamycin, mitomycin C, cisplatin, or the like), and an immunomodulator (OK-432, Broncasma Berna or the like). In a case where the talc, the povidone-iodine, the curing agent, and the carcinostatic agent are delivered into a pleural cavity, inflammation is caused by a chemical function, and in a recovery process, synechia occurs. In addition, the immunomodulator promotes fibrin deposition from the pleura by an allergic reaction with respect to killed bacterium preparation, and thus, promotes the synechia.

<Manufacturing Method of Biodegradable Sheet>

A manufacturing method for manufacturing a biodegradable sheet like that disclosed here is not particularly limited, and an appropriate method capable of manufacturing a sheet containing the biodegradable resin or the like in which the through-holes having the characteristic size described above are formed can be adopted.

An example of the manufacturing method of the biodegradable sheet 20 includes a method of preparing a fiber containing the biodegradable resin described above, and of manufacturing a sheet in the shape of a mesh by using the fiber. The method of preparing the fiber containing the biodegradable resin is not particularly limited, and examples of the method include an electrospinning method (an electric field spinning method and an electrostatic spinning method), a melt-blowing method, and the like. In accordance with the disclosure here, only one type of the methods may be selected and used, or two or more types of methods may be selected and suitably combined. Here, the electrospinning method is a method of forming a microfiber containing a resin, in a state where a high voltage (for example, approximately 20 kV) is applied between a syringe filled with a solution of the resin and a collector electrode. In a case of adopting such a method, the solution extruded from the syringe is electrically charged and is scattered in an electric field, but a solvent contained in the scattered solution is evaporated over time, and thus, a thinned solute appears. The thinned solute becomes the microfiber containing the resin, and is attached to a collector such as a substrate.

A mesh-like base material containing stainless (SUS) steel is used as the collector of the electrospinning method, and thus, a microfiber containing the biodegradable resin as the thinned solute is attached to a real portion of the mesh, and therefore, a mesh containing the microfiber is formed. A resin mesh obtained as described above is peeled off from the mesh-like base material, and thus, it is possible to manufacture the biodegradable sheet according to the invention. It is possible to control the shape of the biodegradable sheet (the hole diameter and the pitch of the through-hole) containing the resin mesh to be manufactured, by suitably adjusting the size of the mesh-like base material (the hole diameter and the pitch).

In addition, similarly, a method of forming a through-hole after obtaining a resin sheet having a homogeneous thickness by scattering the solution described above on the surface of a flat base material that is not in the shape of a mesh such that the microfiber is attached thereto can also be adopted as another example of the manufacturing method using the electrospinning method. In this case, for example, it is possible to form the through-hole in an irradiation site by irradiating the resin sheet with laser light condensed by using a condenser lens. Then, it is possible to control the shape of the biodegradable sheet (the hole diameter and the pitch of the through-hole) containing the resin mesh to be manufactured, by adjusting the energy or an irradiation time of the laser light to be emitted, the interval of the irradiation sites, and the like.

As still another example of the manufacturing method of the biodegradable sheet, the biodegradable sheet according to the invention may be manufactured by spinning the fiber containing the biodegradable resin described above in accordance with an ordinary method, and by knitting a fiber that is obtained into the shape of a mesh.

<<Application of Medical Apparatus (Biodegradable Sheet)>>

The medical apparatus (the biodegradable sheet) disclosed here can be used as an adhesion promoting device that is used for promoting the adhesion of the biological tissue.

A specific type of disease (surgery) to which the medical apparatus (the biodegradable sheet) disclosed here can be applied as the adhesion promoting device is not particularly limited, and the medical apparatus (the biodegradable sheet) can also be applied to any disease (surgery) in which it is preferable for a living body to promote the adhesion through the biodegradable sheet. Among them, on an anatomical form (in terms of the positional relationship between organs that are anastomosed during surgery), in surgery involving the digestive canal (subtotal esophagectomy to treat esophagus cancer, pancreatoduodenectomy to treat pancreatic cancer, colectomy to treat colorectal cancer, and the like) in which circulation disorder is easily caused and there is no means for improving circulation, in order to prevent the ruptured suture in the anastomosis site, it is preferable to apply the medical apparatus (the biodegradable sheet) disclosed here to the anastomosis site following or resulting from surgeries such as those mentioned above by way of example, as the adhesion promoting device.

Hereinafter, various modification examples of the embodiment disclosed above will be described. In the description below, aspects such as the configuration and the like that are not particularly mentioned can be the same as those in the embodiment described above, and a detailed description of such aspects is not repeated.

Modification Example 1

Figure 4:
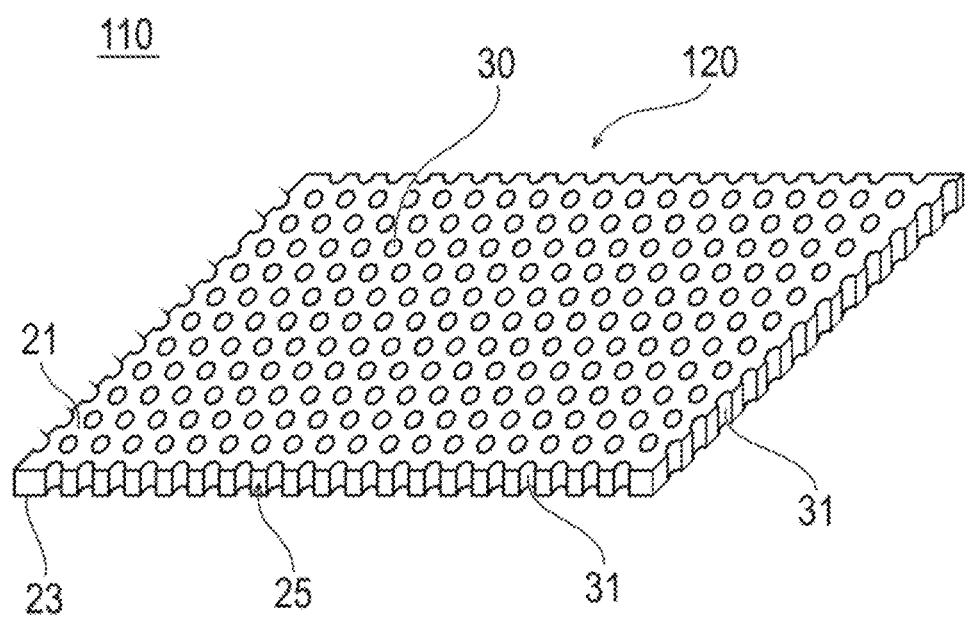
FIG. 4 is an overview perspective view of a biodegradable sheet according to Modification Example 1 of the embodiment.

FIG. 4 illustrates a medical apparatus 110 (a biodegradable sheet 120) according to Modification Example 1.

In the medical apparatus 110 according to Modification Example 1, communicating holes 31 that are exposed to a lateral surface or side surface 25 (i.e., the lateral surface intersecting the one surface 21 and the other surface 23) of the biodegradable sheet 120 are formed. The communicating holes 31, for example, may be or may not be communicated with the through-holes 30 penetrating through one surface 21 and the other surface 23 of the biodegradable sheet 120. In addition, in a case where the biodegradable sheet 120 has an approximately rectangular outer shape, the communicating holes 31 may be formed in only one lateral surface 25 of the four lateral surfaces 25, or the communicating holes 31 may be formed in a plurality of the lateral surfaces 25 out of the four lateral surfaces 25. A specific shape (the shape in a front view), the size, and the like of the communicating hole 31 are not particularly limited.

With the biodegradable sheet 120 according to this modification example, in a case where the communicating holes 31 are formed in the lateral surface(s) 25, a contact area with a living body increases, and thus, more robust adhesion can be attained.

Modification Example 2

Figure 5:
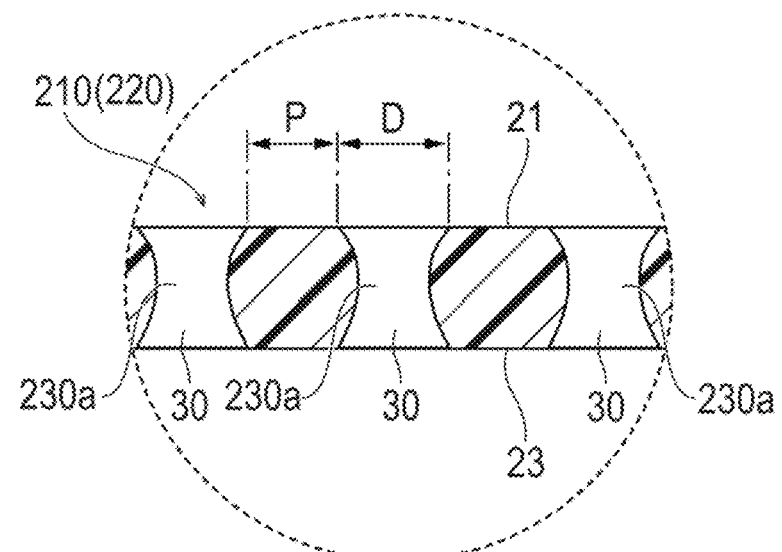
FIG. 5 is an enlarged view of a part of a sectional surface of a biodegradable sheet according to Modification Example 2 of the embodiment.

FIG. 5 illustrates an enlarged sectional view (a sectional view corresponding to FIG. 2) of a medical apparatus 210 (a biodegradable sheet 220) according to Modification Example 2.

As illustrated in FIG. 5, the through-holes 30 formed in the biodegradable sheet 220 have a shape in which a part widens in a direction intersecting with a thickness direction of the biodegradable sheet 220 (an up-down direction of FIG. 5). Specifically, as illustrated in FIG. 5, the through-holes 30 have a sectional shape in which the diameter is gradually narrowed from both the one surface 21 and the other surface 23 towards the approximately central position in the thickness direction. Accordingly, the through-holes 30 include a narrow portion 230a that has a diameter smaller than other portions in the vicinity of the approximately central position in the thickness direction of the biodegradable sheet 220. That is, as shown in FIG. 5, the inner diameter of the through-holes 30 varies along the axial extent of the through-holes, with the inner diameter of the through-holes being greater adjacent the opposite surfaces 21, 23 of the biodegradable sheet 220 than the axial center of the through-holes.

The Hole Diameter/Pitch ratio (D/P) of the biodegradable sheet 220 according to this modification example can also be calculated by the same technique as described above.

With the biodegradable sheet 220 according to this modification example, in a case where the through-hole 30 is formed to include the narrow portion 230a, it is possible to reliably fill the through-holes with a smaller amount of biological component.

Modification Example 3

Figure 6:
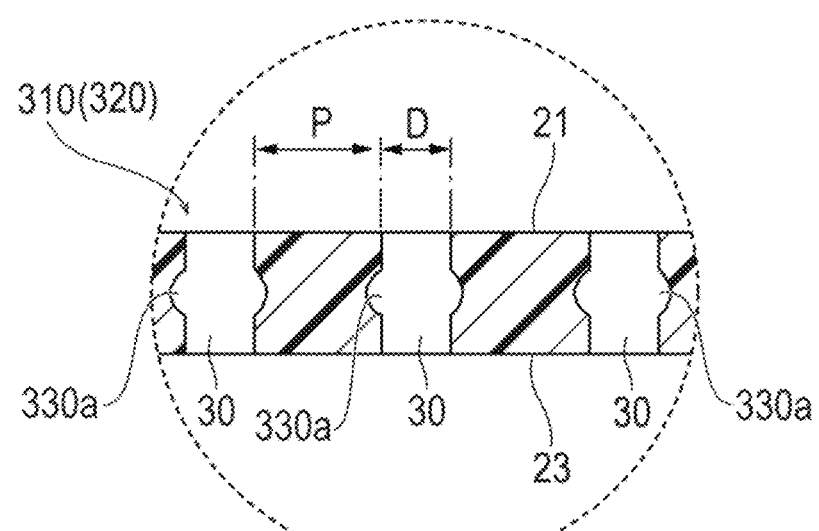
FIG. 6 is an enlarged view of a part of a sectional surface of a biodegradable sheet according to Modification Example 3 of the embodiment.

FIG. 6 illustrates an enlarged sectional view (a sectional view corresponding to FIG. 2) of a medical apparatus 310 (a biodegradable sheet 320) according to Modification Example 3.

As illustrated in FIG. 6, the through-holes 30 have a shape in which a part of the through-holes 30 widens in a direction intersecting with a thickness direction of the biodegradable sheet 320 (an up-down direction of FIG. 6). Specifically, as illustrated in FIG. 6, in the approximately central position in a thickness direction of the through-hole 30, a part of the through-holes 30 widens in the direction intersecting with the thickness direction. Accordingly, a wide portion 330a that is formed to include a diameter larger than other portions in the approximately central position in the thickness direction of the biodegradable sheet 220 is formed in the through-hole 30. That is, as seen in FIG. 5, the inner diameter of the through-holes 330 is greater at the axial center of the through hole than portions of the through-holes 330 adjacent the opposite surfaces of the biodegradable sheet 320.

The Hole Diameter/Pitch ratio (D/P) of the biodegradable sheet 320 according to this modification example can also be calculated by the same technique as described above.

In the medical apparatus 310 according to this modification example, in a case where the through-hole 30 is formed to include the widened portion 330a, it is possible to accumulate a larger amount of biological components, and thus, it is possible to attain more robust adhesion.

Modification Example 4

Figure 7:
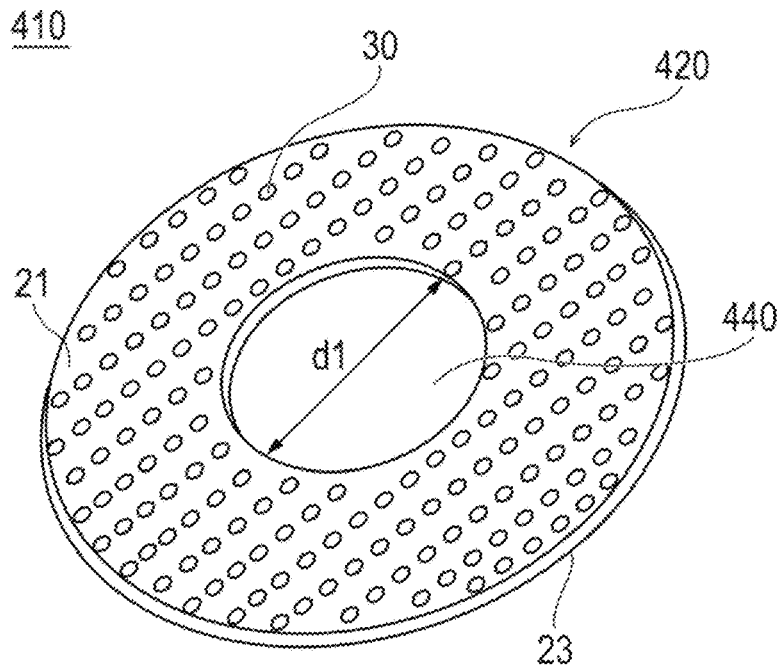
FIG. 7 is an overview perspective view of a biodegradable sheet according to Modification Example 4 of the embodiment.

FIG. 7 illustrates an overview perspective view of a medical apparatus 410 (a biodegradable sheet 420) according to Modification Example 4.

As illustrated in FIG. 7, the biodegradable sheet 420 has a circular shape in a plan view. In addition, the biodegradable sheet 420 includes a central hole 440 that is formed to have a hole diameter d1 larger than that of all of the through-holes 30, in the approximately central position in the plan view.

The central hole 440, for example, can have a hole diameter of 5 mm to 25 mm. In addition, the outer shape of the central hole 440, for example, can be a true-circular shape, and may be an elliptical shape or a rectangular shape, other shapes, or the like.

With the medical apparatus 410 according to this modification example, in a case where the biodegradable sheet 420 has a circular shape in a plan view, and includes the central hole 440 that has the hole diameter d1 larger than that of the through-hole 30, in the approximately central position in the plan view, it is possible to preferably use the biodegradable sheet 420 in a predetermined procedure (for example, colorectal anastomosis using an automatic anastomosis device provided with a trocar and an anvil). In a case of using the biodegradable sheet 420 in the procedure described above, for example, the biodegradable sheet 420 is set such that the central hole 440 is inserted into the trocar of the automatic anastomosis device. Then, the trocar and the anvil are engaged with each other in a state where the biodegradable sheet 420 is set in the trocar, and thus, it is possible to dispose the biodegradable sheet 420 between the intestinal walls of the intestinal canal that is an anastomosis target.

Modification Example 5

Figure 8:
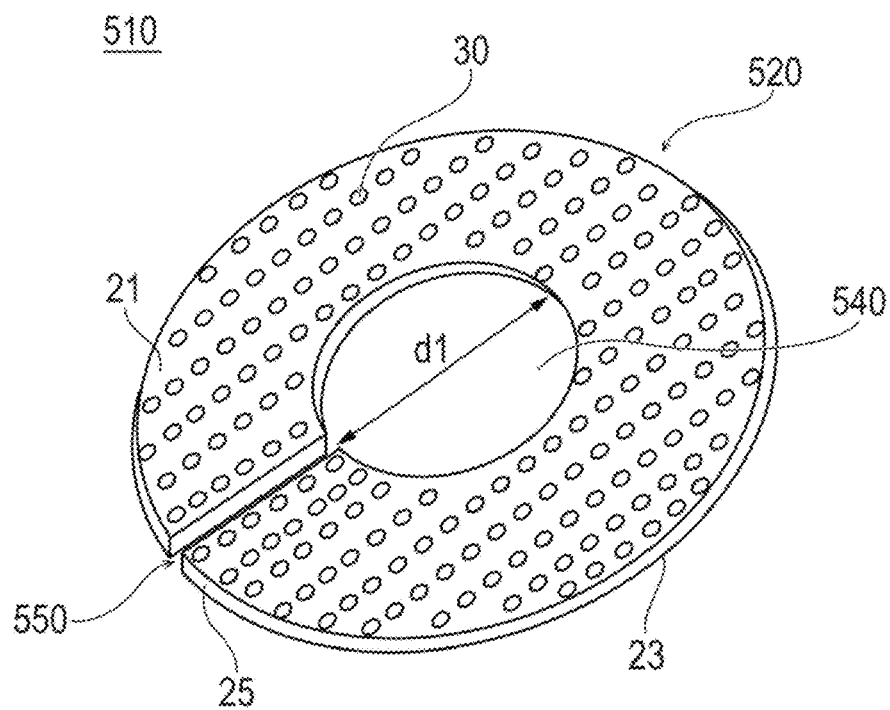
FIG. 8 is an overview perspective view of a biodegradable sheet according to Modification Example 5 of the embodiment.

FIG. 8 illustrates an overview perspective view of a medical apparatus 510 (a biodegradable sheet 520) according to Modification Example 5.

As illustrated in FIG. 8, the biodegradable sheet 520 has a circular shape in a plan view. In addition, the biodegradable sheet 520 includes a central hole 540 that has the hole diameter dl larger than that of the through-hole 30, in the approximately central position in the plan view. In addition, the biodegradable sheet 520 includes a slit 550 continuing to the lateral surface 25 of the biodegradable sheet 520 and the central hole 540. That is, the slit 550 extends radially from the central hole 540 to the lateral surface 25 of the biodegradable sheet 520.

The central hole 540, for example, can have a hole diameter of 1 mm to 20 mm. In addition, the slit 550, for example, can have a linear shape, and may alternatively be in a shape in which curves and straight lines meander (a zigzag shape), or the like, in a plan view.

In the medical apparatus 510 according to this modification example, in a case where the biodegradable sheet 520 has a circular shape in a plan view, and includes the central hole 540 that has the hole diameter dl larger than that of the through-hole 30, in the approximately central position in the plan view, and also includes the slit 550, the biodegradable sheet 520 may preferably be used in a predetermined procedure (pancreatic parenchyma-jejunum seromuscular anastomosis). In a case of using the biodegradable sheet 520 in the procedure described above, for example, the biodegradable sheet 520 is retained on the pancreatic parenchyma side by allowing the ductus pancreaticus exposed from the pancreatic parenchyma to pass through the slit 550. In a state where the biodegradable sheet 520 is retained as described above, an anastomotic surface (a cutoff surface) of the pancreatic parenchyma is moved close to the jejunum (the jejunum with a small hole into which the ductus pancreaticus is inserted) that is an anastomosis target, and thus, it is possible to dispose the biodegradable sheet 520 between the jejunum and the pancreatic parenchyma. The jejunum and the pancreatic parenchyma are sutured in a state where the biodegradable sheet 520 is disposed therebetween, and thus, it is possible to perform the anastomosis.

Modification Example 6

Figure 9:
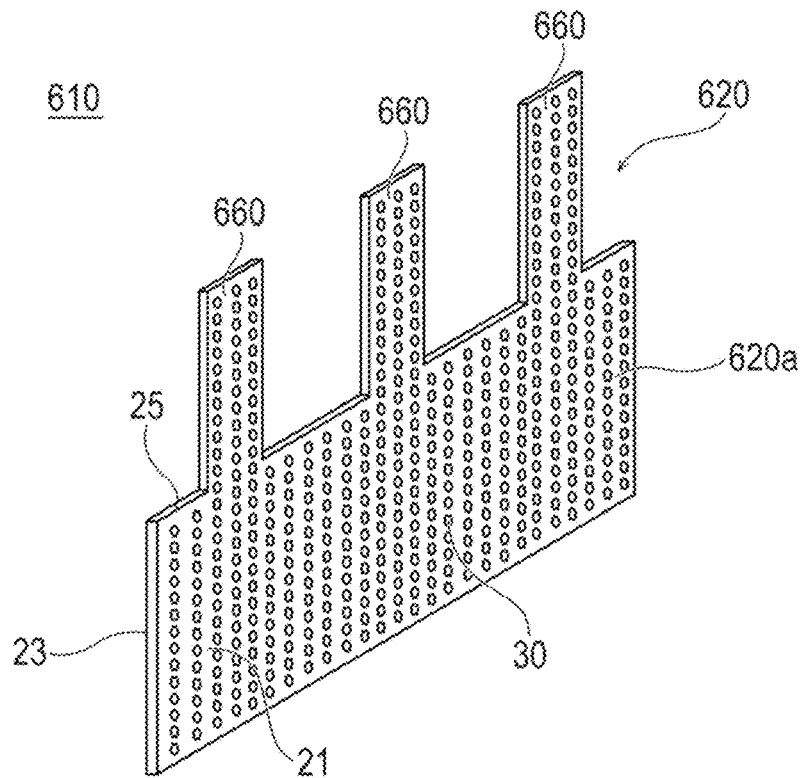
FIG. 9 is an overview perspective view of a biodegradable sheet according to Modification Example 6 of the embodiment.

FIG. 9 illustrates an overview perspective view of a medical apparatus 610 (a biodegradable sheet 620) according to Modification Example 6.

As illustrated in FIG. 9, the biodegradable sheet 620 according to Modification Example 6 includes a main body portion 620a having an approximately rectangular shape in a plan view. In addition, the biodegradable sheet 620 includes a protruding portion 660 protruding from one side (the lateral surface 25) of the main body portion 620a.

A plurality of protruding portions 660, for example, can be provided on one lateral surface 25 of the main body portion 620a. That is, the protruding portions 660 protrude away from one of the lateral surfaces of sides 25 of the main body portion 620a. In addition, any number of protruding portions 620, for example, can be provided on each of a plurality of lateral surfaces 25 of the main body portion 620a. In this modification example, three protruding portions 660 are provided on one lateral surface 25 of the main body portion 620a. The shape of the protruding portion 660, the length of the protruding direction, a width in a direction intersecting the protruding direction, a pitch between the protruding portions 660, and the like, are not particularly limited.

With the medical apparatus 610 according to this modification example, in a case where the biodegradable sheet 620 has a rectangular shape in a plan view, and includes the protruding portion 660 protruding from one side of the biodegradable sheet 620, the biodegradable sheet 620 may preferably be used in a predetermined procedure (triangular anastomosis of the esophagus). In a case of using the biodegradable sheet 620 in the procedure described above, for example, a support string is applied to the end portions of the esophagus (the end portions of the esophagus in a cutoff state) that is an anastomosis target and is lifted, and thus, the protruding portion 660 is allowed to pass through a gap between the support strings. Then, the end portions of the esophagus, facing each other through the main body portion 620a of the biodegradable sheet 620, are sutured. Hereinafter, similarly, an operation of lifting the support string and of allowing the protruding portion 660 to pass through the gap between the support strings is performed in a different position in a circumferential direction of the end portion of the esophagus. By performing the operation described above, the end portions of the esophagus are sutured in three sites in the circumferential direction of the end portion of the esophagus.

Modification Example 7

Figure 10:
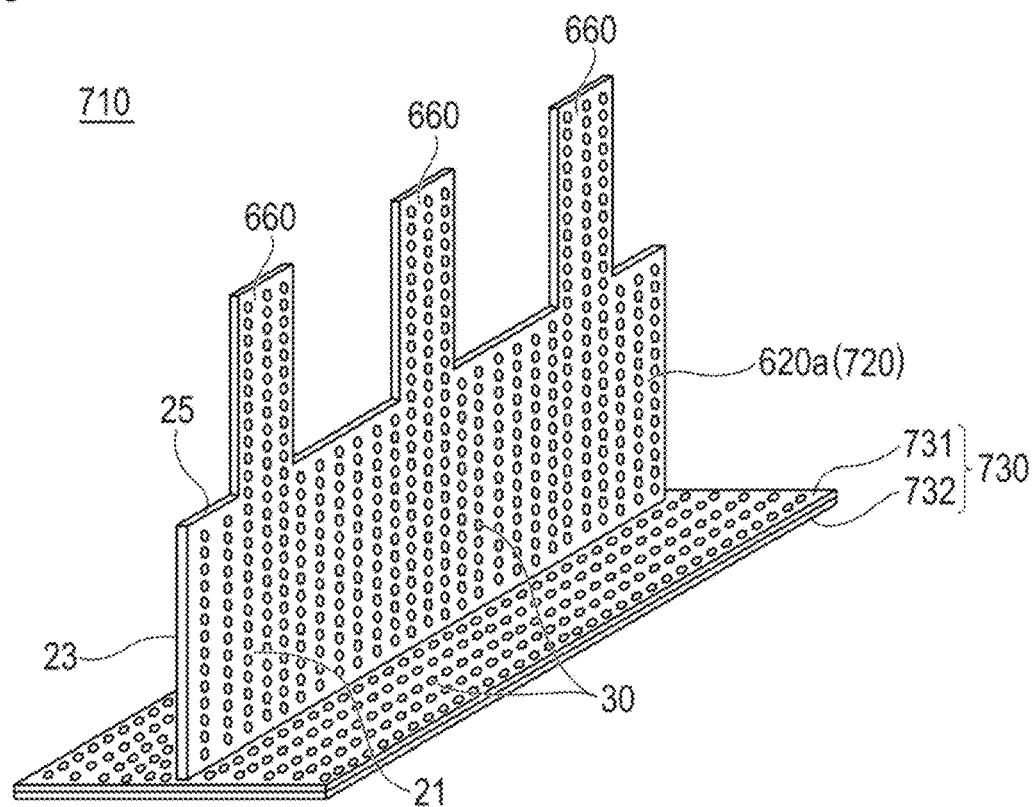
FIG. 10 is an overview perspective view of a biodegradable sheet according to Modification Example 7 of the embodiment.

FIG. 10 illustrates an overview perspective view of a medical apparatus 710 according to Modification Example 7.

As illustrated in FIG. 10, the medical apparatus 710 according to Modification Example 7 includes the main body portion 620a including the biodegradable sheet 720, the protruding portion 660, and a guide portion 730. The main body portion 620a and the protruding portion 660 can be configured substantially the same as those of the medical apparatus 610 according to Modification Example 6 described above.

The guide portion 730 includes a first sheet member 731 in which the through-holes 30 are formed, and a second sheet member 732 that is stacked with respect to the first sheet member 731. The second sheet member 732 does not include through-holes 30.

The second sheet member 732, for example, can be configured to have rigidity (have hard physical properties) higher than that of the first sheet member 731. As an example, the first sheet member 731 and the second sheet member 732 contain or are made of the same material as that of the main body portion 620a, and the through-holes 30 are formed in the first sheet member 731, and thus, it is possible to adjust a relationship between the magnitude of the rigidity of the first sheet member 731 and the magnitude of the rigidity of the second sheet member 732.

The medical apparatus 710 according to this modification example, for example, may preferably be used in triangular anastomosis of the esophagus. The guide portion 730 of the medical apparatus 710 is disposed on the outer circumference side of the esophagus that is an anastomosis target, and thus, is attached to the outer wall of the end portion of the esophagus. The guide portion 730 is in contact with the outer wall of the end portion of the esophagus, and thus, it is possible to position the main body portion 620a on the lumen side of the esophagus. In addition, when the end portions of the esophagus are sutured, and a surplus portion of the medical apparatus 710 is ablated along with a part of the esophagus, the guide portion 730 disposed on the outer wall side of the end portion of the esophagus functions as a guide for designating an ablation position. For this reason, it is possible to smoothly perform an ablation operation.

The guide portion 730, for example, may have a structure not including the first sheet member 731. The guide portion 730 includes at least the second sheet member 732 having a rigidity higher than that of the first sheet member 731, and thus, it is possible to preferably exhibit a function of guiding the ablation position. However, in a case where the guide portion 730 includes the first sheet member 731, it is possible to more preferably promote the adhesion of the esophagus by disposing the first sheet member 731 to be in contact with the outer circumference side of the end portion of the esophagus that is an anastomosis target.

Modification Example 8

Figure 11:
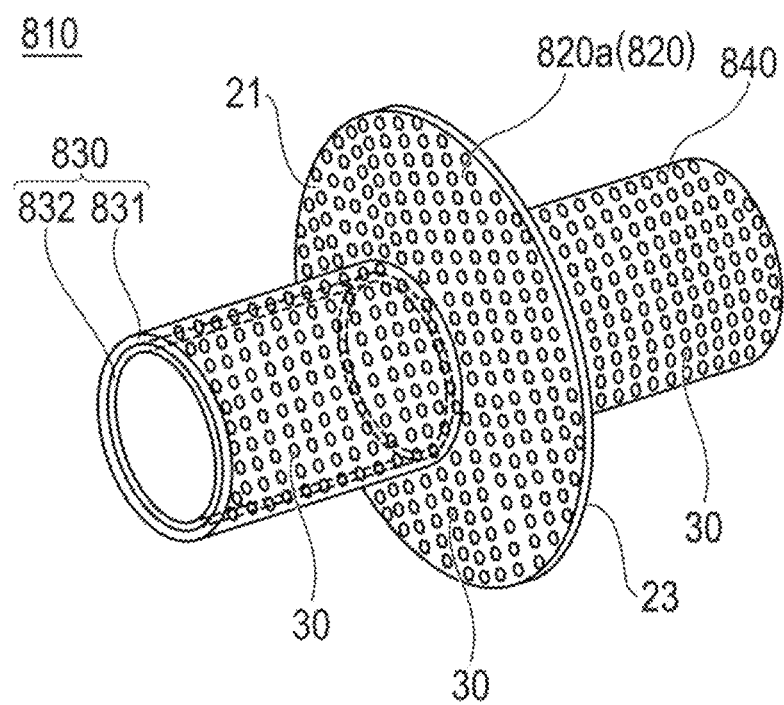
FIG. 11 is an overview perspective view of a biodegradable sheet according to Modification Example 8 of the embodiment.

FIG. 11 illustrates an overview perspective view of a medical apparatus 810 according to Modification Example 8.

As illustrated in FIG. 11, the medical apparatus 810 according to Modification Example 8 includes a main body portion 820a including a biodegradable sheet 820, a first hollow portion 830 protruding to one end side of the main body portion 820a, and a second hollow portion 840 protruding to the other end side of the main body portion 820a.

The first portion 830 includes an approximately cylindrical outer member 831 in which the through-holes 30 are formed, and an approximately cylindrical inner member 832 disposed on the inner surface of the outer member 831.

The outer member 831 and the inner member 832 contain or are made of the same material as that of the biodegradable sheet 820. However, the inner member 832 does not include through-holes. A flow path in which body fluid (pancreatic juice or the like) can be circulated is formed in the lumen of the inner member 832.

The second portion 840 is formed substantially the same as the outer member 831. The second portion 840 contains or is made of the same material as that of the biodegradable sheet 820, and has the through-holes 30.

The medical apparatus 810 according to this modification example, for example, may preferably be used in pancreatic parenchyma-jejunum seromuscular anastomosis. The first portion 830 of the medical apparatus 810, for example, can be inserted into an opening portion formed in the jejunum. The outer member 831 of the first portion 830 is disposed by being attached to the jejunum, and thus, the adhesion with respect to the jejunum is promoted. On the other hand, the through-holes 30 are not formed in the inner member 832 of the first portion 830, and thus, it is possible to prevent collapse or kink. For this reason, it is possible to maintain the flow path formed by the lumen of the inner member 832 in a suitable shape, and it is possible to preferably prevent the occurrence of stenosis due to the narrowing of the lumen of the inner member 832. The main body portion 820a can be disposed to be interposed between the jejunum and the pancreatic parenchyma. In addition, the second portion 840 can be inserted into the ductus pancreaticus. The through-holes 30 are formed in the main body portion 820a and the second portion 840, and thus, it is possible to preferably promote the adhesion in the jejunum, the pancreatic parenchyma, and the ductus pancreaticus.

Aspects of each of the modification examples described above can be suitably combined. For example, the communicating holes 31 formed in the lateral surface 25 described in Modification Example 2 can also be formed in the biodegradable sheets 410, 510, and 610 described in Modification Examples 5, 6, and 7. In addition, for example, through-holes including the narrow portion 230a described in Modification Example 3 and the wide portion 330a described in Modification Example 4 can also be formed in one biodegradable sheet, and the narrow portion 230a and the wide portion 330a can also be provided in one through-hole.

EXAMPLES

The effects of the medical device disclosed here will be described by using the following examples and comparative examples.

However, the technical scope of the invention is not limited only to the following examples.

<Manufacturing Example of Biodegradable Sheet (Adhesion Promoting Device)>

A biodegradable sheet (an adhesion promoting device) in which a plurality of through-holes were formed, as illustrated in FIG. 1 and FIG. 2, was manufactured by irradiating a biodegradable resin sheet formed by an electrospinning method with laser light. Here, the values of the hole diameter (D), the pitch (P), the Hole Diameter/Pitch ratio (D/P), and the thickness (T) of the plurality of through-holes formed in the obtained biodegradable sheet (adhesion promoting device) are shown in Table 1 described below.

An adhesion promoting effect of the biodegradable sheet (the adhesion promoting device) manufactured as described above was evaluated by using a rabbit abdominal wall cecum synechia model.

Specifically, a female Japanese white rabbit) (3±0.5 kg) was prepared as a model animal. As a surgical procedure, the peritoneum was subjected to midline section along a white line on the abdominal wall to have a length of 10 cm, and then, a deficit of 3 cm×4 cm, including the parietal peritoneum and the muscular layer, was prepared on both right and left abdominal walls from a position separated from a midline by 1 cm. Then, four corners of a size of 2 cm×3 cm were sutured by a string, and thus, the abdominal wall and the cecum were fixed.

The biodegradable sheet (the adhesion promoting device) manufactured as described above was interposed between the abdominal wall and the cecum in a fixing portion by using such an abdominal wall cecum synechia model, without imparting damage to the fixing portion. Then, autopsy was performed after 3 days (72 hours) during which the brittleness of a biological tissue after a surgery reached a peak, and the degree of synechia at this time was evaluated in accordance with the following grades. The results are shown in Table 1 described below. In this example, the value of the grade in each test example is an arithmetic average value of values obtained by performing the same test with respect to each of the model animals of the numbers (total 18 heads) shown in Table 1 described below. In addition, in the abdominal wall cecum synechia model, in a non-procedure group subjected to the same test without using the biodegradable sheet, the degree of synechia after 3 days (72 hours) was Grade 0. In addition, in a damaged group subjected to the same test after imparting damage to the fixing portion instead of using the biodegradable sheet, the degree of synechia after 3 days (72 hours) was Grade 3.

Grade 0: No synechia is observed (peeled off under its own weight)

Grade 1: Synechia that can be peeled off by a slight blunt manipulation or procedure without any tissue damage Grade 2: Synechia that can be peeled off by a blunt manipulation or procedure without any tissue damage Grade 3: Synechia that can be peeled off by a blunt manipulation or procedure with tissue damage Grade 4: Synechia that can be peeled off by a strong blunt manipulation or procedure with tissue damage Grade 5: Synechia that is not capable of being peeled off even by a strong blunt manipulation or procedure

TABLE 1

| | Hole diameter D (mm) | Pitch P (mm) | Hole diameter/ pitch ratio D/P | Thickness T (mm) | Synechia grade | Numbers |
|---|---|---|---|---|---|---|
| Example 1 | 0.3 | 0.1 | 3 | 0.1 | 3 | 2 |
| Example 2 | 0.6 | 0.2 | 3 | 0.1 | 3 to 3.5 | 5 |
| Example 3 | 0.6 | 0.2 | 3 | 0.2 | 4 to 5 | 3 |
| Example 4 | 0.6 | 0.4 | 1.5 | 0.1 | 3.5 to 4 | 3 |
| Example 5 | 0.6 | 0.4 | 1.5 | 0.2 | 4 | 1 |
| Example 6 | 1.0 | 0.2 | 5 | 0.2 | 4 | 1 |
| Example 7 | 4.0 | 0.2 | 20 | 0.2 | 4 | 2 |
| Comparative Example 1 | 8.0 | 0.2 | 40 | 0.2 | 2 | 1 |

From the results shown in Table 1, it is found that an excellent adhesion promoting effect can be obtained by the adhesion promoting device using the medical apparatus (the biodegradable sheet) according to the disclosure here in which the value of the Hole Diameter/Pitch ratio (D/P) is 0.25 or more and less than 40 (in particular, 1.5 or more and 20 or less).

<Manufacturing Example of Biodegradable Sheet (Adhesion Promoting Device) Containing Adhesion Enhancement Agent>

A biodegradable sheet (an adhesion promoting device) in which a plurality of through-holes were formed, as illustrated in FIG. 1 and FIG. 2, was manufactured by using two types of formulations. In the first formulation, the biodegradable sheet (an adhesion promoting device) was manufactured by a method in which a biodegradable resin sheet formed by an electrospinning method in a state where an adhesion enhancement agent was dissolved or suspended in a resin solution was subjected to press hole processing (hereinafter, also referred to as a "kneading method"). In the second formulation, the biodegradable sheet (an adhesion promoting device) was manufactured by a method in which a biodegradable resin sheet formed by an electrospinning method only with a resin solution was subjected to press hole processing, and then, was immersed in a solution of an adhesion enhancement agent, and was dried, and thus, the adhesion enhancement agent was adsorbed on the biodegradable sheet (hereinafter, also referred to as an "adsorption method").

Here, the hole diameters (D) of the plurality of through-holes provided in the biodegradable sheet (the adhesion promoting device) containing the obtained adhesion enhancement agent were unified at 0.6 mm, the pitches (P) were unified at 0.2 mm, and the thicknesses (T) were unified at 0.1 mm. The type of adhesion enhancement agent, a blending ratio, and a manufacturing method are shown in Table 2 described below. The value of the blending ratio of the adhesion enhancement agent represents a blending amount of the adhesion enhancement agent by mass % when the mass of the biodegradable sheet is 100 mass %.

An adhesion promoting effect of the biodegradable sheet (the adhesion promoting device) containing the adhesion enhancement agent manufactured as described above was evaluated by using the rabbit abdominal wall cecum synechia model described above.

TABLE 2

| | Adhesion enhancement agent | Blending ratio (%) | Manufacturing method | Synechia grade | Numbers |
|---|---|---|---|---|---|
| Example 8 | Talc | 50 | Kneading method | 5 | 2 |
| Example 9 | Povidone-iodine | 50 | | 4.5 | 1 |
| Example 10 | | 73 | Adsorption method | 5 | 1 |
| Example 11 | Talc/povidone-iodine | 67/8 | | 5< | 1 |
| Example 12 | Minocycline | 21 | | 4.5 | 1 |
| Comparative Example 2 | — | — | — | 4 | 2 |

From the results shown in Table 2, it is found that an excellent adhesion promoting effect is obtained by the adhesion promoting device using the medical apparatus (the biodegradable sheet) containing the adhesion enhancement agent.

As described above, the medical apparatus disclosed here provides a way of reducing the risk of a ruptured suture after a surgery or the like by a simple technique, and is extremely clinically useful.

The detailed description above describes embodiments of a medical apparatus and an adhesion promoting device representing examples of the inventive medical apparatus and adhesion promoting device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An adhesion promoting medical device configured to be interposed between anastomosis sites in a living body, the adhesion promoting medical device comprising:
a biodegradable sheet fabricated from a biodegradable resin, the biodegradable sheet possessing opposite surfaces and including a plurality of spaced-apart through-holes passing through the biodegradable sheet so that the plurality of spaced-apart through-holes open to the opposite surfaces of the biodegradable sheet;
the biodegradable sheet also possessing an outer periphery, the plurality of through-holes being spaced inwardly from the outer periphery of the biodegradable sheet;
each of the through-holes possessing a hole inner diameter D and an outer periphery, a straight line distance between the outer periphery of each of the plurality of spaced-apart through-holes and an adjacent one of the plurality of spaced-apart through-holes being a pitch P of the through-hole;
a ratio (D/P) of the hole inner diameter D to the pitch P of each of the plurality of spaced-apart through-holes is 1.5 or more and less than 40;
application of the adhesion promoting device between the anastomosis sites causes a biological reaction to induce expression of a biological component which accumulates from both of the opposite surfaces of the biodegradable sheet to the plurality of spaced-apart through-holes to thereby promote adhesion at the anastomosis sites; and
each of the plurality of spaced-apart through-holes having an axial extent in a thickness direction of the biodegradable sheet, the inner diameter of at least some of the plurality of spaced-apart through-holes being greater adjacent the opposite surfaces of the biodegradable sheet than an axial center of the biodegradable sheet.

2. The adhesion promoting medical device according to claim 1, further comprising additional through holes passing through the biodegradable sheet so that the additional through-holes open to the opposite surfaces of the biodegradable sheet, the additional through holes being positioned along and intersecting the outer periphery of the biodegradable sheet so that an interior of each of the additional through holes opens to the outer periphery of the biodegradable sheet.

3. The adhesion promoting medical device according to claim 1, wherein each of the plurality of spaced-apart through-holes has an axial extent in a thickness direction of the biodegradable sheet, the inner diameter of at least some of the plurality of spaced-apart through-holes varying along the axial extent of the at least some of the plurality of spaced-apart through-holes.

4. The adhesion promoting medical device according to claim 1, wherein the biodegradable sheet is a circularly-shaped biodegradable sheet in plan view, the circularly-shaped biodegradable sheet including a central hole in addition to the plurality of spaced-apart through-holes, the central hole being positioned in a center of the circularly-shaped biodegradable sheet and passing through the circularly-shaped biodegradable sheet so that the central hole opens to the opposite surfaces of the biodegradable sheet, the central hole possessing an inner diameter larger than the inner diameter of each of the plurality of spaced-apart through-holes.

5. The adhesion promoting medical device according to claim 4, further comprising a slit extending from the central hole to the outer periphery of the circularly-shaped biodegradable sheet, the slit passing completely through the circularly-shaped biodegradable sheet so that the slit opens to the opposite surfaces of the biodegradable sheet.

6. The adhesion promoting device according to claim 1, wherein the hole diameter D is 0.1 mm to 6 mm, and the pitch P is 0.1 mm to 0.4 mm.

7. An adhesion promoting medical device configured to be interposed between anastomosis sites in a living body, the adhesion promoting medical device comprising:
a biodegradable sheet fabricated from a biodegradable resin, the biodegradable sheet possessing opposite surfaces and including a plurality of spaced-apart through-holes passing through the biodegradable sheet so that the plurality of spaced-apart through-holes open to the opposite surfaces of the biodegradable sheet;
the biodegradable sheet also possessing an outer periphery, the plurality of through-holes being spaced inwardly from the outer periphery of the biodegradable sheet;
each of the through-holes possessing a hole inner diameter D and an outer periphery, a straight line distance between the outer periphery of each of the plurality of spaced-apart through-holes and an adjacent one of the plurality of spaced-apart through-holes being a pitch P of the through-hole;
a ratio (D/P) of the hole inner diameter D to the pitch P of each of the plurality of spaced-apart through-holes is 1.5 or more and less than 40;
application of the adhesion promoting device between the anastomosis sites causes a biological reaction to induce expression of a biological component which accumulates from both of the opposite surfaces of the biodegradable sheet to the plurality of spaced-apart through-holes to thereby promote adhesion at the anastomosis sites; and
wherein each of the plurality of spaced-apart through-holes has an axial extent in a thickness direction of the biodegradable sheet, the inner diameter of at least some of the plurality of spaced-apart through-holes being greater at an axial center of the through hole than at portions of the through-hole adjacent the opposite surfaces of the biodegradable sheet.

8. The adhesion promoting device according to claim 7, wherein the hole diameter D is 0.1 mm to 6 mm.

9. The adhesion promoting device according to claim 7, wherein the pitch P is 0.1 mm to 0.4 mm.

10. The adhesion promoting device according to claim 7, wherein a thickness of the biodegradable sheet is 0.1 mm to 0.2 mm.

11. The adhesion promoting device according to claim 7, wherein each of the through-holes is provided approximately perpendicularly along a thickness direction of the biodegradable sheet.

12. The adhesion promoting device according to claim 7, wherein each of the through-holes has a shape in which a part widens in a direction intersecting with the thickness direction of the biodegradable sheet.

13. The adhesion promoting device according to claim 7, wherein the biodegradable sheet has a circular shape in a plan view, and a central hole having a hole diameter larger than that of the through-hole is formed in an approximately central position in the plan view.

14. The adhesion promoting device according to claim 13, further comprising: a slit continuing to a lateral surface of the biodegradable sheet and the central hole.

15. The adhesion promoting device according to claim 7, wherein the biodegradable sheet includes a main body portion formed in an approximately rectangular shape in a plan view, and a projection portion protruding from the main body portion is formed on one side of the main body portion.

16. The adhesion promoting device according to claim 7, wherein a constituent material of the biodegradable sheet is a polylactic acid (PLA), a polyglycolic acid (PGA), or a lactic acid-glycolic acid copolymer (PLGA).

17. The adhesion promoting device according to claim 7, wherein an adhesion enhancement agent is blended in the biodegradable sheet.

18. A method comprising:
    interposing a biodegradable sheet between anastomosis sites in a living body following a surgical procedure;
    the biodegradable sheet that is interposed between the anastomosis sites possessing opposite surfaces and including a plurality of spaced-apart through-holes passing through the biodegradable sheet so that the plurality of spaced-apart through-holes open to the opposite surfaces of the biodegradable sheet, each of the plurality of the through-holes possessing a hole inner diameter D, a straight line distance between the outer periphery of each of the plurality of spaced-apart through-holes and an adjacent one of the plurality of spaced-apart through-holes being a pitch P of the through-hole;
    the biodegradable sheet that is interposed between the anastomosis sites being configured so that a ratio (D/P) of the hole inner diameter D to the pitch P of each of the plurality of through-holes is 0.25 or more and less than 40; and
    the biodegradable sheet that is interposed between the anastomosis sites causing a biological reaction that induces expression of a biological component that is accumulated from both of the opposite surfaces of the biodegradable sheet to the through-holes to promote adhesion at the anastomosis sites.

19. The method according to claim 18, wherein the hole inner diameter of each of the plurality of the through-holes is 0.1 mm to 6 mm.

20. The method according to claim 18, wherein the biodegradable sheet that is positioned at the anastomosis site is configured so that a ratio (D/P) of the hole inner diameter D to the pitch P of each of the plurality of through holes is 1.5 or more and less than 40.

21. The method according to claim 18, wherein the surgical procedure includes surgery involving a digestive canal in a living body, and the anastomosis site at which the biodegradable sheet is positioned is along the digestive canal.

* * * * *